(12) United States Patent
Carlsson

(10) Patent No.: US 12,734,297 B2
(45) Date of Patent: Sep. 15, 2026

(54) MEDICAMENT DELIVERY DEVICE

(71) Applicant: SHL MEDICAL AG, Zug (CH)

(72) Inventor: Daniel Carlsson, Enskede (SE)

(73) Assignee: SHL Medical AG, Zug (CH)

( * ) Notice: Subject to any disclaimer, the term of this patent is extended or adjusted under 35 U.S.C. 154(b) by 504 days.

(21) Appl. No.: 18/278,702

(22) PCT Filed: Dec. 21, 2021

(86) PCT No.: PCT/EP2021/086923
§ 371 (c)(1),
(2) Date: Aug. 24, 2023

(87) PCT Pub. No.: WO2022/207137
PCT Pub. Date: Oct. 6, 2022

(65) Prior Publication Data

US 2024/0139418 A1 May 2, 2024

(30) Foreign Application Priority Data

Mar. 31, 2021 (EP) .................................... 21166376

(51) Int. Cl.
*A61M 5/24* (2006.01)
*A61M 5/315* (2006.01)

(52) U.S. Cl.
CPC ..... *A61M 5/2425* (2013.01); *A61M 2005/244* (2013.01); *A61M 2005/31518* (2013.01); *A61M 2205/02* (2013.01); *A61M 2205/3592* (2013.01)

(58) Field of Classification Search
CPC .......... A61M 5/2425; A61M 2005/244; A61M 2005/31518
See application file for complete search history.

(56) References Cited

U.S. PATENT DOCUMENTS

| | | | |
|---|---|---|---|
| 4,019,655 | A | 4/1977 | Moeller |
| 2020/0297580 | A1 | 9/2020 | Liscio |

FOREIGN PATENT DOCUMENTS

| | | | |
|---|---|---|---|
| WO | 2007/038091 | A2 | 4/2007 |
| WO | 2011/075042 | A1 | 6/2011 |
| WO | 2011/133823 | A1 | 10/2011 |
| WO | 2020/143987 | A1 | 7/2020 |

OTHER PUBLICATIONS

International Search Report and Written Opinion for Int. App. No. PCT/EP2021/086923, mailed Feb. 10, 2022.

*Primary Examiner* — Bradley J Osinski
(74) *Attorney, Agent, or Firm* — McDonnell Boehnen Hulbert & Berghoff LLP

(57) ABSTRACT

A medicament delivery device is presented for expelling medicament from a mechanically flexible medicament container where the delivery device has a housing having a proximal housing end, a distal housing end, and a central channel extending through the proximal housing end and towards the distal housing end, the central channel being configured to receive the medicament container, wherein the housing has an inner surface provided with a first axial channel and a second axial channel arranged on opposite sides of the central channel, a drive member arranged to move linearly towards the proximal end of the housing, a plurality of first segments arranged one after the other in the first axial channel, and a plurality of second segments arranged one after the other in the second axial channel, wherein the drive member has a first leg and a second leg are configured to move.

20 Claims, 4 Drawing Sheets

21a
3
3d 3e
21
9
1
11d
11a
23c
11
3c
23a
23d
21c
27
13
13a
13c
13d
23e
11c
11b
19
21b
25
13b
17
23b
5
15
23f
13b
20
13a
7

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2021/086923 filed Dec. 21, 2021, which claims priority to European Patent Application No. 21166376.0 filed Mar. 31, 2021. The entire disclosure contents of these applications are herewith incorporated by reference into the present application.

TECHNICAL FIELD

The present disclosure generally relates to a medicament delivery device for expelling medicament from a flexible medicament container.

BACKGROUND

Some liquid chambers may be mechanically flexible or soft. A blow-fill-seal (BFS) container is an example of a common type of flexible container containing liquid.

BFS containers generally comprise a liquid chamber filled with a liquid. In some cases, BFS containers may also comprise a gas-filled chamber in fluid communication with the liquid chamber.

Today, BFS containers filled with a medicament are typically handled manually by the user during administration. This means that the user has to compress the liquid chamber or the gas-filled chamber manually to expel the medicament from the BGF container. This is typically done by medical professionals to ensure that the dose is administered correctly.

SUMMARY

It would be desirable to automate the medicament expulsion process from BFS containers, or similar flexible medicament containers, to facilitate patients to administer the medicament themselves.

An object of the present disclosure is thus to provide a medicament delivery device which solves, or at least mitigates, problems of the prior art.

There is hence provided a medicament delivery device for expelling medicament from a mechanically flexible medicament container, the medicament delivery device comprising: a housing having a proximal housing end, a distal housing end, and a central channel extending through the proximal housing end and towards the distal housing end, the central channel being configured to receive the medicament container, wherein the housing has an inner surface provided with a first axial channel and a second axial channel arranged on opposite sides of the central channel, each of the first axial channel and the second axial channel opening into the central channel, a drive member having a first leg extending into the first axial channel via the distal end of the first axial channel and a second leg extending into the second axial channel via the distal end of the second axial channel, the drive member being arranged to move linearly towards the proximal housing end, a plurality of first segments arranged one after the other in the first axial channel, and a plurality of second segments arranged one after the other in the second axial channel, wherein the first leg and the second leg are configured to move a respective one of the first segments and the second segments towards the proximal housing end when the drive member is moved linearly towards the proximal housing end, whereby at least one of the first segments and at least one of the second segments are moved radially towards each other into the central channel to thereby subject the medicament container to oppositely directed radial forces.

The first segments and the second segments can thus squeeze medicament from the medicament container. The medicament delivery device can thus facilitate medicament administration for users.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the components thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the term "longitudinal", "longitudinally", "axially" or "axial" refer to a direction extending from the proximal end to the distal end, typically along the device or components thereof in the direction of the longest extension of the device and/or component.

Similarly, the terms "transverse", "transversal" and "transversally" refer to a direction generally perpendicular to the longitudinal direction.

Further, the terms "circumference", "circumferential", "circumferentially" refer to a circumference or a circumferential direction relative to an axis, typically a central axis extending in the direction of the longest extension of the device and/or component. Similarly, "radial" or "radially" refer to a direction extending radially relative to the axis, and "rotation", "rotational" and "rotationally" refer to rotation relative to the axis.

According to one example, the segment of the first segments which is closest to the proximal housing end is a first leading end segment and the segment of the second segments which is closest to the proximal housing end is a second leading end segment, wherein the at least one first segment includes the first leading end segment and the at least one second segment includes the second leading end segment.

According to one embodiment the first segments are connected to each other and to the first leg, and the second segments are connected to each other and to the second leg. Reloading of the drive member after medicament expulsion may thereby be facilitated. Assembly of the device may also thereby be facilitated. As the drive member is moved in the distal direction during reloading, the first segments and the second segments will follow in their respective axial channel. The medicament delivery device may thus be reusable.

Further, the connection of the first segments to each other and the second segments to each other can prevent the segments from uncontrollably falling into the central channel.

According to one embodiment the first segments are connected to each other and to the first leg by means of a string or by means of magnetism.

According to one embodiment the second segments are connected to each other and to the second leg by means of a string or by means of magnetism.

According to one embodiment each of the first axial channel and the second axial channel have a proximal end, a distal end, and a proximal end guide portion via which the respective axial channel transitions into the central channel, wherein the proximal end guide portions each define a plane that intersects the central channel, and wherein the at least one of the first segments and the at least one of the second segments are moved radially towards each other into the central channel via a respective one of the inclined proximal end guide portions.

According to one embodiment the first segments and the second segments have the shape of spheroids or polyhedrons.

The shape of the first segments and the second segments may generally be any shape that allows for the segments to move relative to each other in three dimensions when the drive member is moved towards the proximal housing end.

One embodiment comprises a sleeve fixedly arranged in the central channel and configured to receive a portion of the medicament container, the sleeve comprising radially flexible arms extending towards the proximal housing end, the arms being configured to engage with the medicament container to thereby fixate the medicament container axially in the housing.

According to one embodiment the arms comprise radially inwards extending protrusions configured to engage with the medicament container.

The radially inwards extending protrusions may in a direction towards the distal direction first increase in radial thickness and then decrease in radial thickness. In a longitudinal section of the sleeve, the radially inwards extending protrusions may have a triangular or wedge shape. This can facilitate the arms in flexing radially outwards when the medicament container is slid into and out of the medicament delivery device through the central channel. The arms may thereby engage with and disengage from the medicament container.

One embodiment comprises a resilient member resting on a distal end face of the sleeve and configured to bias the drive member in a direction towards the distal housing end.

The medicament delivery device may be a manual device or an autoinjector.

The drive member may thus for example be manually driven, spring-driven, or driven by an electric motor.

In the case that the medicament delivery device is manual, the drive member may protrude from a distal end of the housing. The drive member may be moved in the proximal direction by manual force applied by the user onto a distal drive member end of the drive member.

One embodiment comprises a medicament container detector mechanical switch arranged to be actuated by insertion of the medicament container between the arms.

The medicament container detector mechanical switch may be arranged to extend radially towards the centre of the central channel.

One embodiment comprises an RFID reader configured to be activated by switching the medicament container detector switch.

According to one embodiment the RFID reader is axially positioned in the housing to read an RFID tag of the medicament container when the medicament container has been received between the arms. The medicament delivery device can thereby read data from the RFID tag. Such data may for example be one or more of a medicament expiry date, batch ID, and medicament container ID.

One embodiment comprises a transmitter configured to wirelessly transmit data obtained from the RFID tag. The transmitter may for example be configured to transmit the data to a smart phone, tablet computer, or to the cloud.

One embodiment comprises a medicament delivery detection mechanical switch configured to be actuated by linear movement of the drive member towards the proximal housing end.

The medicament delivery device may comprise a timer circuit which is activated by actuation of the medicament delivery detection mechanical switch.

The timer circuit may be configured to count down from or up to a predetermined number when activated. The predetermined number may be the time it takes to deliver the medicament from the medicament delivery device.

The medicament delivery device may comprise a display which displays information about the time left of medicament delivery, based on the counting of the timer circuit.

Generally, all terms used in the claims are to be interpreted according to their ordinary meaning in the technical field, unless explicitly defined otherwise herein. All references to "a/an/the member, apparatus, component, means, etc." are to be interpreted openly as referring to at least one instance of the member, apparatus, component, means, etc., unless explicitly stated otherwise.

BRIEF DESCRIPTION OF THE DRAWINGS

The specific embodiments of the presently disclosed concept will now be described, by way of example, with reference to the accompanying drawings, in which.

DETAILED DESCRIPTION

The presently disclosed concept will now be described more fully hereinafter with reference to the accompanying drawings, in which exemplifying embodiments are shown. The presently disclosed concept may, however, be embodied in many different forms and should not be construed as limited to the embodiments set forth herein; rather, these embodiments are provided by way of example so that this disclosure will be thorough and complete, and will fully convey the scope of the presently disclosed concept to those skilled in the art. Like numbers refer to like members throughout the description.

Figures 1, 2:
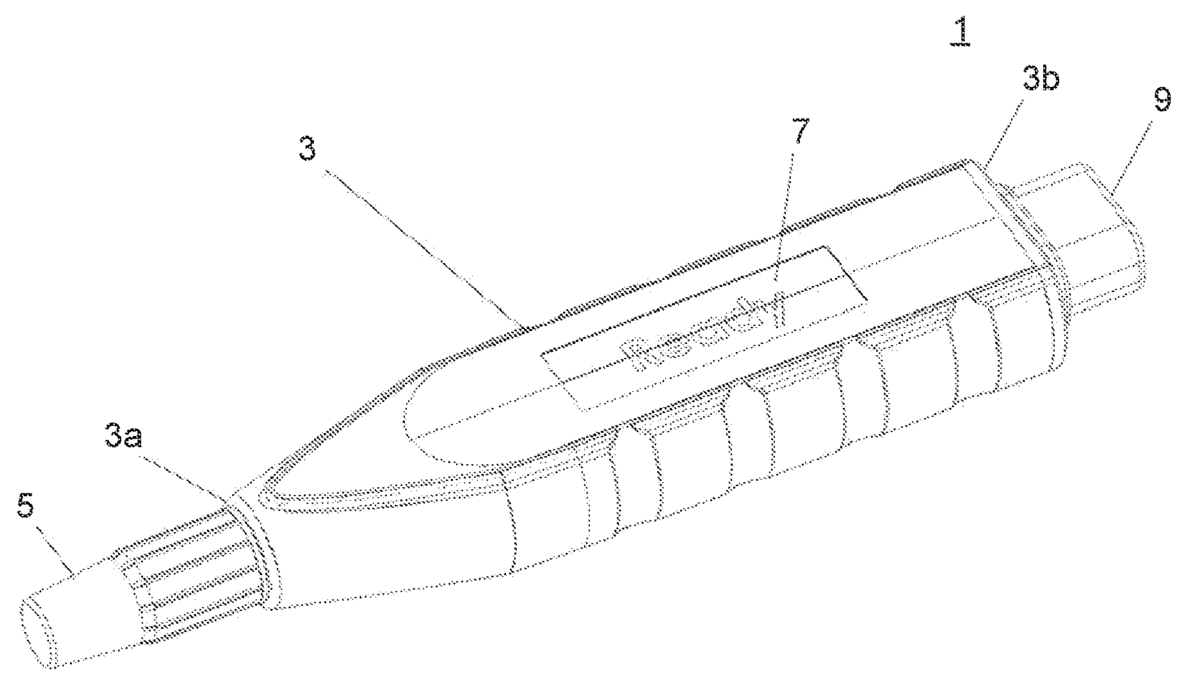
FIG. 1 is a perspective view of an example of a medicament delivery device.
FIG. 2 is an exploded view of the medicament delivery device in FIG. 1.

FIG. 1 shows a perspective view of an example of a medicament delivery device 1. The exemplified medicament delivery device 1 is reusable but could alternatively be disposable.

The medicament delivery device 1 comprises a housing 3. The housing 3 has a proximal housing end **3*a* and a distal housing end 3*b*. The proximal housing end 3*a* and the distal housing end 3*b* form opposite ends of the housing 3 along the longitudinal axis of the medicament delivery device 1**.

The medicament delivery device 1 is configured to expel medicament from a mechanically flexible medicament container. The mechanically flexible medicament container may for example be a BFS container.

The mechanically flexible medicament container has a removable cap 5 forming a proximal end of the medicament delivery device 1 when the medicament delivery device 1 has been loaded with the mechanically flexible medicament container.

The mechanically flexible medicament container may be provided with a delivery member such as a needle. The cap 5 covers the delivery member when it is attached to the main body of the mechanically flexible medicament container.

The medicament delivery device 1 comprises a drive member arranged in the housing 3. The drive member may have a distal drive member end 9 extending from the distal housing end 3*b*. The distal drive member end 9 forms a button for triggering medicament delivery.

The medicament delivery device 1 may comprise a display 7 configured to display data for example related to medicament delivery and/or to the medicament contained in the mechanically flexible medicament container.

FIG. 2 shows an exploded view of the medicament delivery device 1. A mechanically flexible medicament container 11 with which the medicament delivery device 1 can be loaded is also depicted.

The medicament container 11 comprises the cap 5 and has a distal body 11*a* comprising a liquid chamber 11*b*. Before use, the liquid chamber 11*b* is filled with a liquid medicament. The exemplified medicament container 11 comprises an end structure 11*c* arranged distally relative to the liquid chamber 11*b*. The medicament container 11 has a waist 11*d* arranged between the liquid chamber 11*b* and the end structure 11*c*.

The end structure 11*c* may optionally include a gas-filled chamber arranged distally relative to the liquid chamber 11*b*. The gas-filled chamber 11*c* may for example be filled with air or an inert gas. The liquid chamber 11*b* and the gas-filled chamber are arranged in fluid communication. Medicament may be expelled by applying radial force onto the liquid chamber 11*b* or the gas-filled chamber 11*c*.

The housing 3 comprises a central channel 3*c*. The central channel 3*c* is an axial channel which extends through the proximal housing end 3*a* towards the distal housing end 3*b*.

According to the example, the housing 3 is provided with a first radial opening 3*d*. The first radial opening 3*d* opens into the central channel 3*c*.

According to the example, the housing 3 comprises a second radial opening 3*e*. The second radial opening 3*e* opens into the central channel 3*c*.

The medicament delivery device comprises a sleeve 13. The sleeve 13 is configured to be arranged in the central channel 3*c*.

The sleeve 13 comprises two radially flexible arms 13*a* extending axially in the proximal direction. The sleeve 13 is configured to receive the end structure 11*c* of the medicament container 11 between the arms 13*a*. Each arm 13*a* has a respective radially inwards extending protrusion 13*b*. The radially inwards extending protrusions 13*b* are configured to be received in the waist 11*d* of the medicament container 11. The arms 13*a* thereby engage with the medicament container 11. The radially inwards extending protrusions 13*b* may be wedge-shaped, or triangular, in a longitudinal section of the sleeve 13, to facilitate reception and removal of the medicament container 11.

The sleeve 13 is configured to engage with the housing 3. The sleeve 13 is thereby typically arranged axially and radially fixed relative to the housing 3, or may alternatively be an integral part of the housing 3.

The sleeve 13 has a radially outwards extending attachment structure 13*c* configured to engage with the second radial opening 3*e* of the housing 3. The radially outwards extending attachment structure 13*c* may be wedge-shaped in a longitudinal section of the sleeve 13, to facilitate assembly of the sleeve 13 with the housing 3. The radially outwards extending attachment structure 13*c* may taper in the proximal direction.

The medicament delivery device 1 comprises a medicament container detector mechanical switch 15. The medicament container detector mechanical switch 15 is configured to extend into the central channel 3*c* through the first radial opening 3*d* of the housing 3. The medicament container detector mechanical switch 15 is arranged to be actuated by insertion of the medicament container 11 in between the arms 13*a* of the sleeve 13.

The medicament delivery device 1 comprises a resilient member 17 configured to rest on a distal end face 13*d* of the sleeve 13. The resilient member 17 may for example be a spring such as a coil spring.

The medicament delivery device 1 comprises a drive member 21 arranged in the housing 3. The drive member 21 is biased in the distal direction by the resilient member 17. The drive member 21 is configured to be moved linearly towards the proximal housing end 3*a*. Medicament is thereby expelled from the medicament container 11, as will be explained in more detail in the following.

The drive member 21 comprises a first leg 21*a* and a second leg 21*b*. The first leg 21*a* and the second leg 21*b* extend axially in the proximal direction.

According to the example, the drive member 21 includes a central leg 21*c* extending axially in the proximal direction. The central leg 21*c* is arranged between the first leg 21*a* and the second leg 21*b*. The resilient member 17 is provided around the central leg 21*c*, biasing the drive member 21 in the distal direction.

The medicament delivery device 1 comprises a plurality of first segments 23*a* arranged proximally of the first leg 21*a*, one after the other in the axial direction. The first segment 23*a* arranged adjacent to a proximal end of the first leg 21*a* is a first trailing end segment 23*c*. The most proximally located first segment 23*a* is a first leading end segment 23*d*.

The first segments 23*a* may for example have the shape of spheroids or polyhedrons. In the present example, the first segments 23*a* are spherical or essentially spherical.

The first segments 23*a* are connected to each other and to the first leg 21*a* in this example, although in some cases some or all of these connections are not necessary. The segments may be connected to each other but not to the leg, for example. The first segments 23*a* may for example be connected to each other and/or to the first leg 21*a* by means of a string or by means of magnetism. In another alternative, two or more of the segments may be a single integral component, for example with the component comprising a plurality of rigid portions alternating with flexible portions.

The medicament delivery device 1 comprises a plurality of second segments 23*b* arranged proximally of the second leg 21*b*, one after the other in the axial direction. The second segment 23*b* arranged adjacent to a proximal end of the second leg 21*b* is a second trailing end segment 23*e*. The most proximally located second segment 23*b* is a second leading end segment 23*f*.

The second segments 23*b* may for example have the shape of spheroids or polyhedrons. In the present example, the second segments 23*b* are spherical or essentially spherical.

The second segments 23*b* are connected to each other and to the second leg 21*b* in this example, although in some cases some or all of these connections are not necessary. The segments may be connected to each other but not to the leg, for example. The second segments 23*b* may for example be connected to each other and to the second leg 21*b* by means of a string or by means of magnetism.

The distal drive member end 9 of the drive member 21 extends distally from the housing 3.

The medicament delivery device 1 comprises a medicament delivery detection mechanical switch 19 configured to be actuated by linear movement of the drive member 21 towards the proximal housing end 3*a*.

The medicament delivery device 1 may comprise a circuit board or substrate 20 configured to be attached to the housing 3. The medicament container detector mechanical switch 15 and the medicament delivery detection mechanical switch 19 may be provided on the circuit board or substrate 20.

The display 7 may be mounted onto the circuit board or substrate 20.

The circuit board or substrate 20 may be provided with an RFID reader (not shown) configured to be activated by switching the medicament container detector switch 15. The medicament delivery device 1 may comprise a transmitter (not shown) configured to wirelessly transmit data obtained by the RFID reader.

The medicament delivery device 1 may comprise a detachable sidewall 25 configured to be protect the circuit board or substrate 20. The sidewall 25 is configured to be attached to the housing 3. The sidewall 25 may have a window in which the display 7 is arranged.

The medicament delivery device 1 may comprise a rear wall 27 configured to be attached to the distal housing end 3*b*. The rear wall 27 is provided with an opening through which the distal drive member end 9 extends distally.

Figure 3:
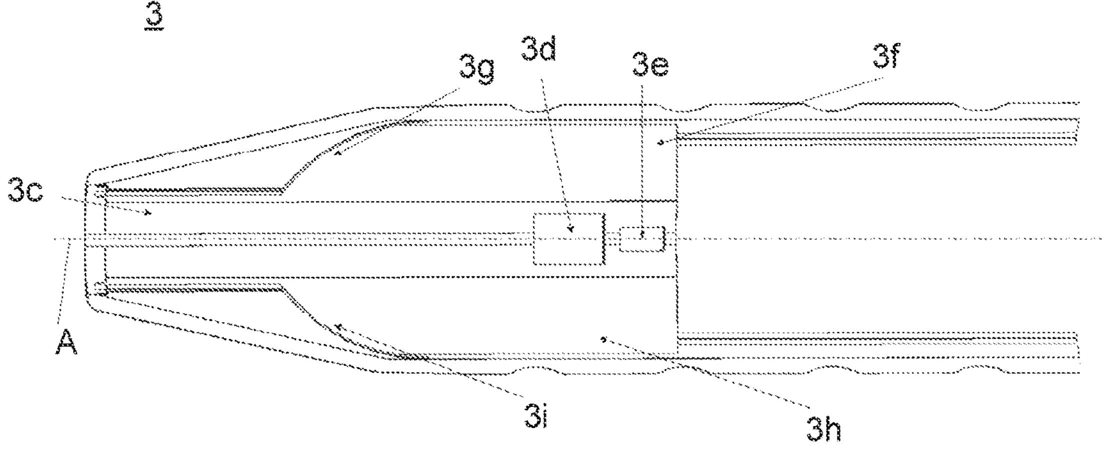
FIG. 3 is a longitudinal section of the housing of the medicament delivery device in FIG. 1.

FIG. 3 shows a longitudinal section of the housing 3. The housing 3 has an inner surface provided with a first axial channel 3*f*, and a second axial channel 3*h* arranged oppositely relative to the first axial channel 3*f*.

The first axial channel 3*f* and the second axial channel 3*h* extend in parallel with the central channel 3*c*. The first axial channel 3*f* and the second axial channel 3*f* open into the central channel 3*c*. Alternatively to extending in parallel, the first axial channel 3*f* and the second axial channel 3*h* could be angled relative to the central channel 3*c*, with the proximal end of the first axial channel 3*f* and the second axial channel 3*h* being closer to the axis than the distal end of the first axial channel 3*f* and the second axial channel 3*h*.

The first axial channel 3*f* has a proximal end and a distal end. The first axial channel 3*f* has a proximal end guide portion 3*g* which is a surface or surfaces via which the first axial channel 3*f* transitions into the central channel 3*c*. The proximal end guide portion 3*g* forms the proximal end of the first axial channel 3*f*. The proximal end guide portion 3*g* may for example be inclined such as curved or formed by one or more discrete step changes in inclination.

The inclined proximal end guide portion 3*g* of the first axial channel 3*f* defines a plane that intersects the central channel 3*c*. The plane thus intersects the central longitudinal axis A of the housing 3.

The second axial channel 3*h* has a proximal end and a distal end. The second axial channel 3*h* has a proximal end guide portion 3*i* which is a surface or surfaces via which the second axial channel 3*h* transitions into the central channel 3*c*. The proximal end guide portion 3*i* forms the proximal end of the second axial channel 3*h*. The proximal end guide portion 3*i* may for example be inclined such as curved or formed by one or more discrete step changes in inclination.

The proximal end guide portions 3*g*, 3*i* could alternatively form a respective transverse or perpendicular surface relative to a central longitudinal axis A of the housing 3.

In the present example, the proximal end guide portion 3*i* of the second axial channel 3*h* are inclined and define a respective plane that intersects the central channel 3*c*. The plane thus intersects the central longitudinal axis A.

The first segments 23*a* are arranged one after the other in the first axial channel 3*f*. The second segments 23*b* are arranged one after the other in the second axial channel 3*h*.

The first leg 21*a* extends into the first axial channel 3*f* from a distal end of the first axial channel 3*f*. The second leg 21*b* extends into the second axial channel 3*h* from a distal end of the second axial channel 3*h*.

Figure 4:
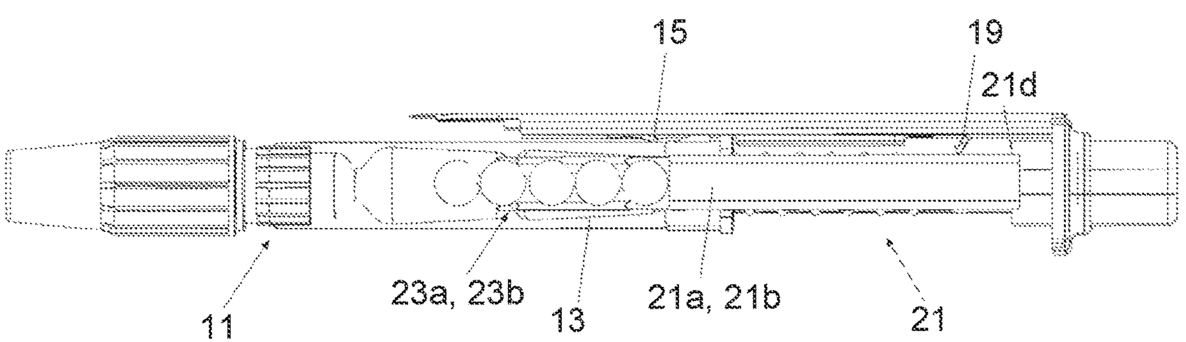
FIG. 4 shows a side view of the medicament delivery device without the housing.

FIG. 4 depicts the medicament delivery device 1 without the housing 3 in a bottom view, showing only one of the first and second segments 23*a*, 23*b*. The medicament delivery device 1 has been loaded with the medicament container 11.

As the medicament container 11 is inserted into the housing 3 via the central channel 3*c*, and is received between the arms 13*a*, the end structure 11*c* physically contacts the medicament container detector mechanical switch 15. The medicament container detector mechanical switch 15 is thereby actuated. The actuation causes the RFID reader to be activated. The medicament container 11, for example the end structure 11*c*, may comprise an RFID tag containing information about the medicament container 11 and/or about the liquid medicament in the liquid chamber 11*b*. When activated, the RFID reader is configured to read data from the RFID tag.

The medicament delivery detection mechanical switch 19 extends into the central channel 3*c*. The drive member 21 has a proximal radial surface which has a radial dimension which is large enough so that it contacts the medicament delivery detection mechanical switch 19 when the drive member 21 is moved linearly in the proximal direction when medicament is to be expelled from the medicament container 11.

The medicament delivery device 1 may comprise a timer circuit (not shown) which is activated to count to a predetermined number when the medicament delivery detection mechanical switch 19 is actuated by the drive member 21. The display 7 may be configured to display information about the time left of medicament delivery, based on the counting of the timer circuit.

The operation of the medicament delivery device 1 will now be described in more detail with reference to FIGS. 5A-5E.

Figure 5A:
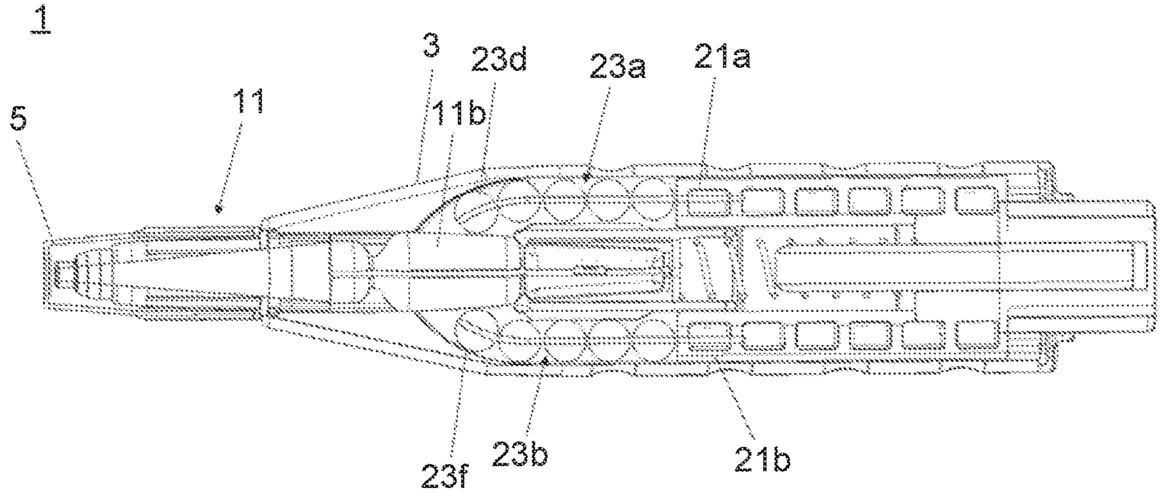
FIGS. 5A, 5B, 5C, 5D and 5E show longitudinal sections of the medicament delivery device during various stages of operation.

FIG. 5A shows the medicament delivery device 1 in an initial default state, when it has been loaded with the medicament container 11 via the central channel 3*c*. The first leading end segment 23*d* and the second leading end segment 23*f* are arranged on opposite sides of the liquid chamber 11*b*, radially outside the liquid chamber 11*b*.

Figure 5B:
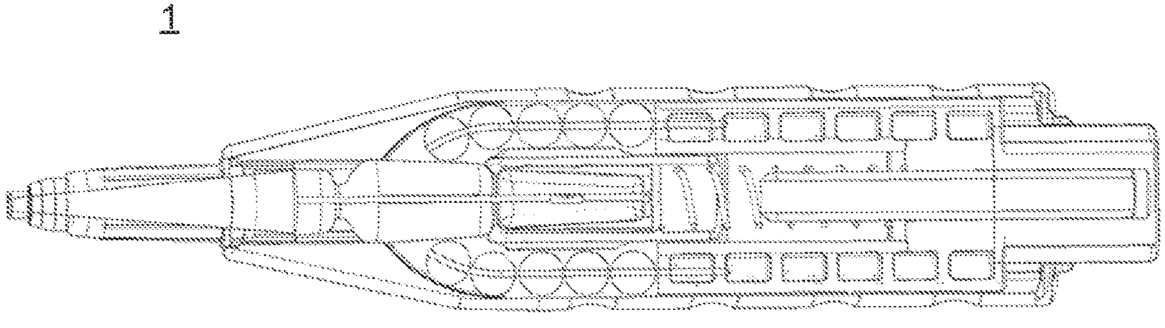

In FIG. 5B, the cap 5 has been removed from the medicament container 11. The medicament delivery device 1 is in this state ready for use.

Figure 5C:
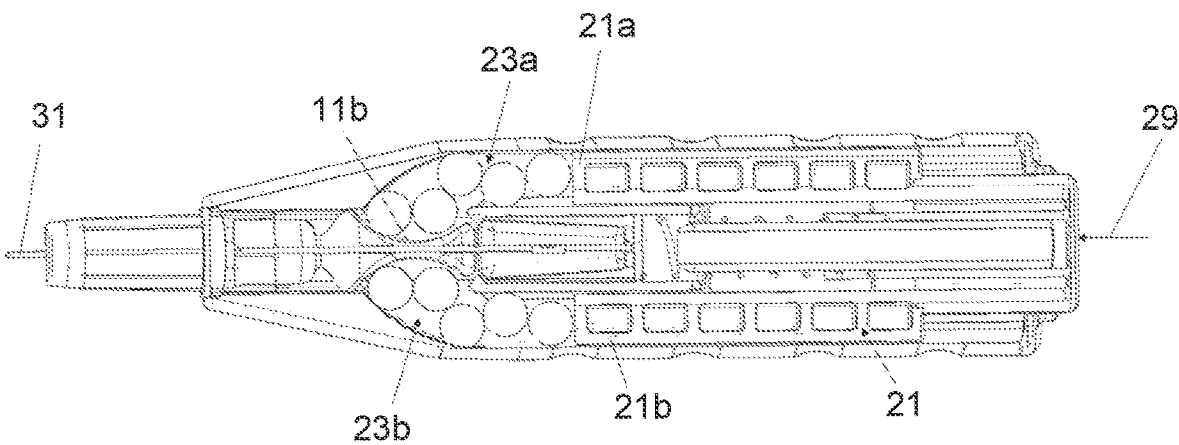

In FIG. 5C, the delivery member 31, in this example a needle, of the medicament container 11 has been exposed. The delivery member 31 may be exposed by removing e.g. a delivery member shield provided under the cap 5 to provide additional protection of the delivery member 31. The delivery member shield may according to some variations be removed together with the cap 5, as it may be attached to the cap 5.

Further, in FIG. 5C the medicament delivery device 1 is shown in a state of medicament delivery. The distal drive member end 9 has been pushed into the housing 3 as shown by the arrow 29. The drive member 21 has thus been moved in the proximal direction towards the proximal housing end 3*a* of the housing 3. The first leg 21*a* thus pushes the first segments 23*a* in the proximal direction and the second leg 21*b* pushes the second segments 23*b* in the proximal direction. The first segments 23*a* are pushed against the inclined proximal end guide portion 3*g* of the first axial channel 3*f* and the second segments 23*b* are pushed against the inclined proximal end guide portion 3*i* of the second axial channel 3*h*. At least the first leading end segment 23*d* and the second leading end segment 23*f* are thus guided to move radially inwards into the central channel 3*c* and act with oppositely directed radial forces on the liquid chamber 11*b* arranged between them. The medicament contained in the liquid chamber 11*b* is thus squeezed out from the liquid chamber 11*b*.

In case e.g. the proximal end guide portions are perpendicular to the central longitudinal axis, another first segment than the first leading end segment and another second segment than the second leading end segment may move radially into the central channel.

Figure 5D:
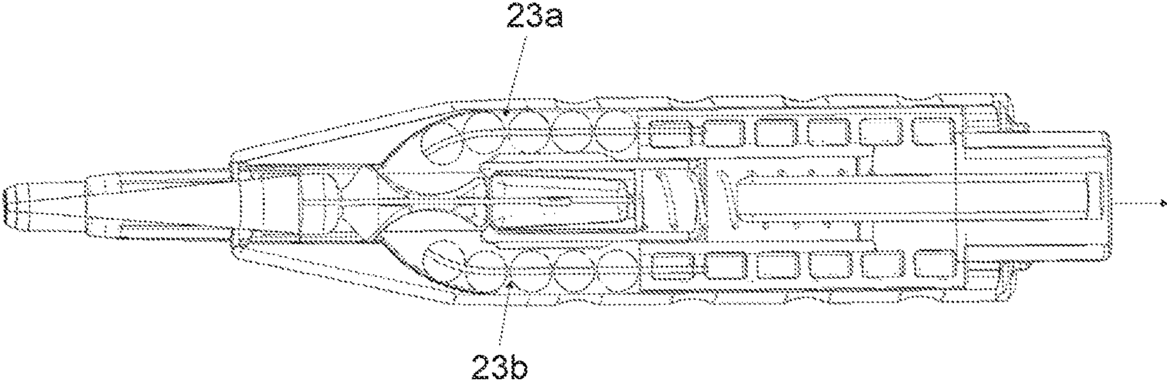

In FIG. 5D, the drive member 21 has been moved back in the distal direction (automatically by the resilient member 17 in this example) after the medicament has been delivered from the medicament container 11. The drive member 21 may alternatively be moved back manually by the user, or, in some variations, automatically for example by means of a motor.

The first segments 23*a*, which are connected to each other, and the second segments 23*b*, which are connected to each other, follow the movement of the drive member 21 because they are connected to the first leg 21*a* and the second leg 21*b*, respectively. The first segments 23*a* and the second segments 23*b* that contacted the liquid chamber 11*b* during medicament delivery are therefore moved radially from the central channel and back into the first axial channel 3*f* and the second axial channel 3*h*. In an example where the segments are not connected to one another (and/or not connected to the legs), gravity could be used to help reset the device, by holding the device with the distal end down while the drive member is moved back in the distal direction.

Figure 5E:
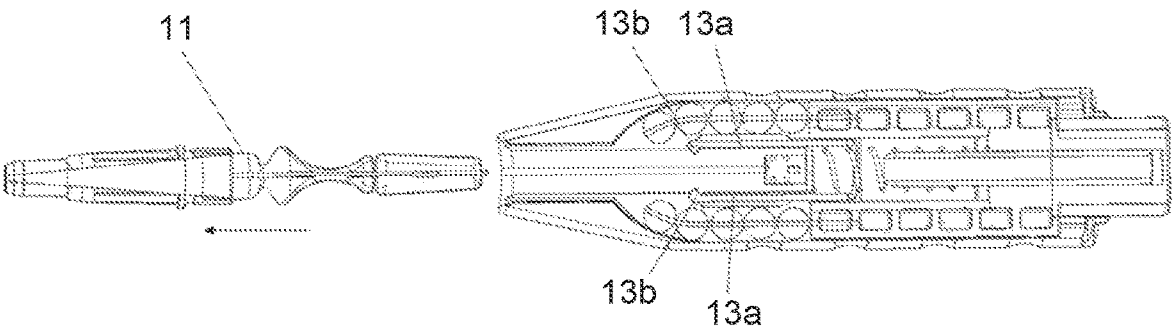

Because the first segments 23*a* and the second segments 23*b* have been moved away from the liquid chamber 11*b*, the medicament container 11 can be removed from the medicament delivery device, as shown in FIG. 5E. The arms 13*a* flex radially outwards due to the shape of the radially inwards extending protrusion 13*b* when the medicament container 11 is pulled out from the housing 3.

After the used medicament container 11 has been removed and discarded, a new medicament container 11 may be placed in the medicament delivery device 1 and the medicament delivery device 1 may thus be reused.

The presently disclosed concept has mainly been described above with reference to a few examples. However, as is readily appreciated by a person skilled in the art, other embodiments than the ones disclosed above are equally possible within the scope of the presently disclosed concept, as defined by the appended claims.

The invention claimed is:

1. A medicament delivery device for expelling medicament from a mechanically flexible medicament container, the medicament delivery device comprising:

a housing having a proximal housing end, a distal housing end, and a central channel extending through the proximal housing end and towards the distal housing end, the central channel being configured to receive the medicament container, wherein the housing has an inner surface provided with a first axial channel and a second axial channel arranged on opposite sides of the central channel, each of the first axial channel and the second axial channel opening into the central channel, a drive member having a first leg extending into the first axial channel via the distal end of the first axial channel and a second leg extending into the second axial channel via the distal end of the second axial channel, the drive member being arranged to move linearly towards the proximal housing end, a plurality of first segments arranged one after the other in the first axial channel, and a plurality of second segments arranged one after the other in the second axial channel, wherein the first leg and the second leg are configured to move a respective one of the first segments and the second segments towards the proximal housing end when the drive member is moved linearly towards the proximal housing end, whereby at least one of the first segments and at least one of the second segments are moved radially towards each other into the central channel to thereby subject the medicament container to oppositely directed radial forces.

2. The medicament delivery device as claimed in claim 1, wherein the first segments are connected to each other and to the first leg, and the second segments are connected to each other and to the second leg.

3. The medicament delivery device as claimed in claim 2, wherein the first segments are connected to each other and to the first leg by means of a string or by means of magnetism.

4. The medicament delivery device as claimed in claim 2, wherein the second segments are connected to each other and to the second leg by means of a string or by means of magnetism.

5. The medicament delivery device as claimed in claim 1, wherein each of the first axial channel and the second axial channel have a proximal end, a distal end, and a proximal end guide portion via which the respective axial channel transitions into the central channel, wherein the proximal end guide portions each define a plane that intersects the central channel, and wherein the at least one of the first segments and the at least one of the second segments are moved radially towards each other into the central channel via a respective one of the inclined proximal end guide portions.

6. The medicament delivery device as claimed in claim 1, wherein the first segments and the second segments have the shape of spheroids or polyhedrons.

7. The medicament delivery device as claimed in claim 1, comprising a sleeve fixedly arranged in the central channel and configured to receive a portion of the medicament container, the sleeve comprising radially flexible arms extending towards the proximal housing end, the arms being configured to engage with the medicament container to thereby fixate the medicament container axially in the housing.

8. The medicament delivery device as claimed in claim 7, wherein the arms comprise radially inwards extending protrusions configured to engage with the medicament container.

9. The medicament delivery device as claimed in claim 7, comprising a resilient member resting on a distal end face of the sleeve and configured to bias the drive member in a direction towards the distal housing end.

10. The medicament delivery device as claimed in claim 7, comprising a medicament container detector mechanical switch arranged to be actuated by insertion of the medicament container between the arms.

11. The medicament delivery device as claimed in claim 10, comprising an RFID reader configured to be activated by switching the medicament container detector switch.

12. The medicament delivery device as claimed in claim 11, wherein the RFID reader is axially positioned in the housing to read an RFID tag of the medicament container when the medicament container has been received between the arms.

13. The medicament delivery device as claimed in claim 11, comprising a transmitter configured to wirelessly transmit data obtained from the RFID tag.

14. The medicament delivery device as claimed in claim 1, comprising a medicament delivery detection mechanical switch configured to be actuated by linear movement of the drive member towards the proximal housing end.

15. A medicament delivery device comprising:

a housing having a proximal housing end, a distal housing end, and a central channel configured as a through hole in the proximal housing end;

a flexible medicament container positioned in the central channel;

a first axial channel and a second axial channel on opposite sides of the central channel and both opening into the central channel;

a drive member having a first leg and a second leg, where the drive member moves linearly relative to the proximal housing end during delivery of medicament from the medicament container;

a plurality of first segments movably positioned in the first axial channel; and a plurality of second segments movably positioned in the second axial channel, wherein axial movement of the drive member causes movement of the plurality of first segments towards the proximal housing end such that at least one of the plurality of first segments and at least one of the plurality of second segments are moved radially towards each other into the central channel subjecting the medicament container to oppositely directed radial forces.

16. The medicament delivery device of claim 15, wherein the plurality of first segments are connected to each other by magnetism.

17. The medicament delivery device of claim 15, wherein the plurality of first segments are spherically shaped.

18. The medicament delivery device of claim 15 further comprises a sleeve located in the central channel, where the sleeve comprises a flexible arm axially fixed to the medicament container.

19. The medicament delivery device of claim 15 further comprising a spring that biases the drive member in a distal direction relative to the housing.

20. The medicament delivery device of claim 15 further comprising an RFID reader and a switch, where insertion of the medicament container into the central channel activates the switch which in turn causes the RFID reader to read an RFID tag.

* * * * *